United States Patent [19]

Melker

[11] Patent Number: 5,628,305

[45] Date of Patent: May 13, 1997

[54] UNIVERSAL VENTILATION DEVICE

[75] Inventor: Richard Melker, Gainesville, Fla.

[73] Assignee: Richard J. Melker, Gainesville, Fla.

[21] Appl. No.: 534,606

[22] Filed: Sep. 27, 1995

[51] Int. Cl.[6] .................................................. A61M 16/00
[52] U.S. Cl. ................... 128/202.29; 128/205.13; 128/205.14; 128/205.15; 128/205.16
[58] Field of Search ..................... 128/202.29, 205.13, 128/205.14, 205.15, 205.16

[56] References Cited

U.S. PATENT DOCUMENTS

| | | | |
|---|---|---|---|
| 1,371,702 | 3/1921 | Lyon | 128/205.18 |
| 2,428,451 | 10/1947 | Emerson | 128/205.13 |
| 3,037,497 | 6/1962 | Roberson | 128/202.29 |
| 3,158,152 | 11/1964 | Bloom | 128/202.29 |
| 3,461,866 | 8/1969 | Ritchie | 128/205.13 |
| 3,515,134 | 6/1970 | Taylor | 128/205.14 |
| 3,537,450 | 11/1970 | Fox | 128/205.14 |
| 3,548,812 | 12/1970 | Kalyaerskaya et al. | 128/205.14 |
| 3,905,362 | 9/1975 | Eyrick et al. | 128/202.22 |
| 3,918,447 | 11/1975 | Inkster et al. | 128/205.18 |
| 3,939,830 | 2/1976 | da Costa | 128/205.18 |
| 4,297,999 | 11/1981 | Kitrell | 128/205.16 |
| 4,493,614 | 1/1985 | Chu et al. | 417/22 |
| 4,643,719 | 2/1987 | Garth et al. | 604/73 |
| 4,782,831 | 11/1988 | Gallant | 128/204.18 |
| 4,836,198 | 6/1989 | Gates | 128/205.18 |
| 4,898,167 | 2/1990 | Pierce et al. | 128/205.16 |
| 5,398,674 | 3/1995 | Martin | 128/203.11 |
| 5,427,091 | 6/1995 | Phillips | 128/202.29 |

FOREIGN PATENT DOCUMENTS

| | | | |
|---|---|---|---|
| 646890 | 8/1962 | Canada | 128/202.29 |
| 934973 | 8/1963 | United Kingdom | 128/202.29 |

*Primary Examiner*—Aaron J. Lewis
*Attorney, Agent, or Firm*—Saliwanchik, Lloyd & Saliwanchik

[57] ABSTRACT

The universal ventilation device, UVD, of this invention is designed to separate the gas (and bodily fluids) of the victim from that of the rescuer and to deliver a known, adjustable volume of gas at a known, adjustable rate. The UVD can be used without other adjuncts, or in combination with a bag-valve device, or a compressed oxygen or compressed air or gas powered device.

11 Claims, 7 Drawing Sheets

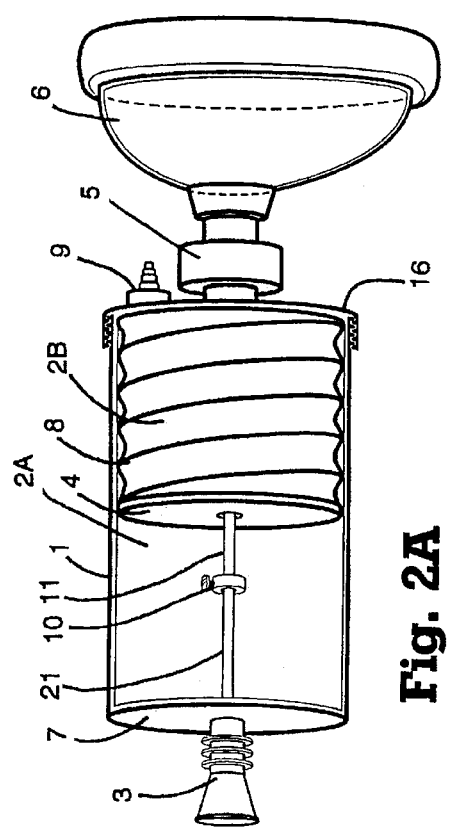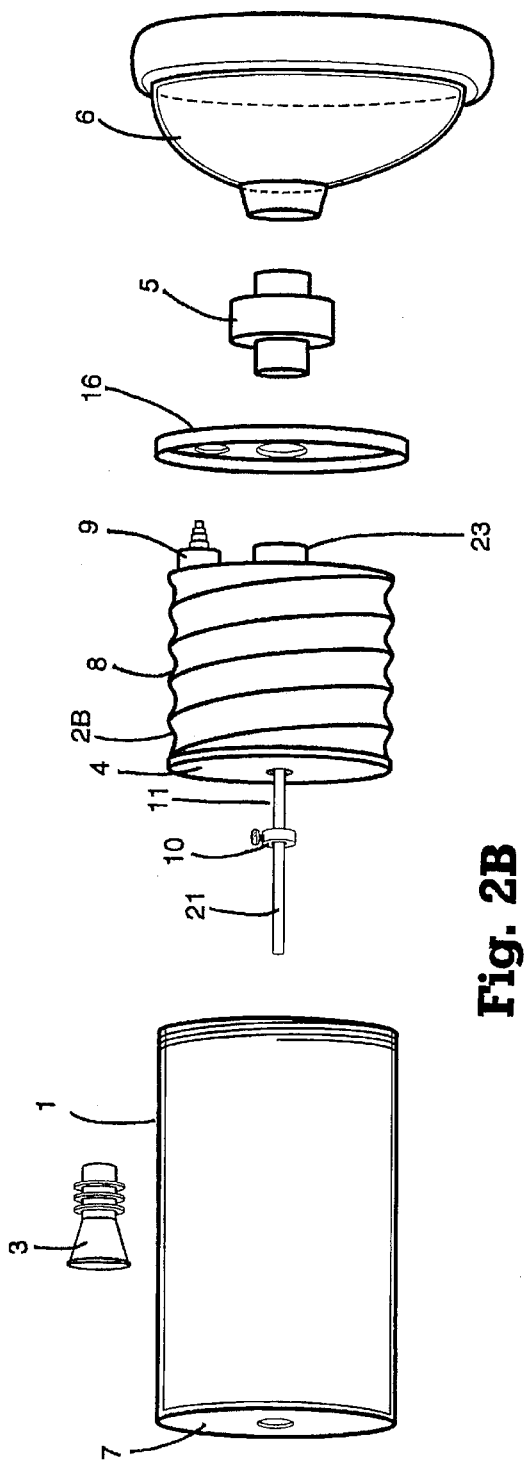

UNIVERSAL VENTILATION DEVICE

FIELD OF THE INVENTION

This invention relates to a novel, universal ventilation device (UVD) which can be used to resuscitate patients without the danger of introducing too much or too little air or gas, or at too rapid or too slow a flow or ventilation rate, to be beneficial to the recipient. The device has a number of advantageous features over known resuscitators, not the least of which are its durability, portability, ease of handling and cleaning, and its low cost.

BACKGROUND OF THE INVENTION

Artificial ventilation is frequently performed by "first responders" and emergency medical technicians prior to the arrival of advanced life support (paramedics). In order to ventilate properly, the breaths must be given slowly and the volume of gas carefully controlled. It is often difficult to gauge the exact volume and flow-rate of gas delivery. Improper ventilation may cause gas to enter the stomach, which may lead to regurgitation of the stomach contents followed by aspiration of the vomitus into the lungs.

A number of ventilation devices have been reported in the art. However, these devices have all suffered from one or another disadvantage or design defect. For example, in early ventilation devices, it was believed that it was desirable not only to provide a source of ventilating air or gas to resuscitate a patient whose independent inspiration of air or gas is interrupted, but to also provide a suction or vacuum to withdraw air or gas from the lungs. It has since come to be generally accepted in the art that this is not the case. First, damage to the lungs may result from the forced expiration of air or gas, while the natural compliance of the lungs and chest cavity is sufficient to result in expulsion of air or gas even though the patient may not be adequately inhaling on their own. Second, problems of regurgitation of stomach contents have been encountered with these vacuum creating devices with the possible complications of fouling of the device, blockage of air or gas passages with masses of partially digested matter, and aspiration of acidic fluids. Aside from this common misapprehension, a number of prior art devices have also suffered from the inability of a single rescuer to easily operate the device alone. Many prior art devices suffer from inadequate control of the rate or volume of gas delivery. Others are simply cumbersome or awkward to operate. A review of prior art devices of which the applicant is aware follows.

U.S. Pat. No. 1,371,702 (the '702 patent) discloses a respirating device which could introduce and remove gases from the lungs of a patient. The device comprised a large cylinder mounted on a base upon which an operator could place a foot while pumping a piston to provide air or gas to the patient. Because of the closed nature of this system, and the belief that victims would need to have air or gas withdrawn for them, the device of the '702 patent does not provide for unassisted exhalation by the victim. The two hands of the rescuer are not available for making the mask seal on the victim.

U.S. Pat. No. 2,428,451 (the '451 patent) discloses a pressure resuscitator in which a bellows, with a handle attached at the upper end of the bellows, is compressed to deliver air or gas through a face-mask to a victim. The bellows is not contained within any type of rigid cylinder, resulting in difficulty for the rescuer to attain proper vertical alignment of the bellows during depression cycles. In addition, the placement of the handle at the upper end of the bellows means that the operator has but one hand to properly seat the face-mask on the face of a victim. Finally, a complex system of valves is described for achieving proper delivery of fresh air or gas to the victim while still allowing the victim to exhale unassisted.

U.S. Pat. No. 3,461,866 (the '866 patent) discloses a two-cylindered manually operated artificial respirator in which on the downward stroke of a handle, air or gas is supplied to a victim from one cylinder, while on the upward stroke, air or gas is withdrawn from the victim. Rate and volume of air or gas delivery is controlled by the operator limiting the rate and amount of pumping handle travel, with pressure relief valves and audible signals being provided in the event that too much air or gas is being presented to or extracted from the lungs.

U.S. Pat. No. 3,905,362 (the '362 patent) discloses a volume-rate respirator system and method wherein a complex electronic and a vertically movable weight driven system provides precise control of inspiration and expiration rates and volumes. The device of the '362 patent would be expensive, poorly portable, and best adapted for non-emergency maintenance use in a hospital context.

U.S. Pat. No. 3,918,447 (the '447 patent) discloses a ventilator particularly adapted for use on neonates in an incubator wherein a piston within a cylinder divides the cylinder into an upper and a lower chamber. A source of pressurized gas supplied to the upper chamber causes the piston to move downward, thereby forcing air or gas in the lower chamber, which has been supplied from a source of breathing gas, to enter the lungs of the patient. There is no provision for portable use of this device.

U.S. Pat. No. 3,939,830 (the '830 patent) discloses a manually operable dechoking and resuscitating device wherein a handle attached to a piston within a cylinder is biased to move downward to expel air or gas trapped within the cylinder below the piston head. The rate at which the piston moves downward is not readily controllable by the rescuer as the biasing means, a spring, has its own characteristic rate of retraction or expansion. Thus, the rate of air or gas delivery by this device in its ventilation mode is not user controllable. In addition, as the piston is drawn upward for the next downward stroke of air or gas expulsion into the patient, a vacuum is created in the patient's lungs thus possibly causing lung damage, regurgitation, and fouling of the instrument as noted above. In a modified embodiment of the '830 device, the downward-biasing spring is removed and a handle is located on the outside of the cylinder. The handle is located at the upper extremity of the cylinder, as opposed to the placement of a handle close to the bottom of the cylinder in one embodiment of the instant invention. The location of the face mask in the '830 device is at the bottom, center of the cylinder, rather than being eccentrically placed toward the periphery as in one embodiment of the instant invention described below. However, the downward, inhalation cycle of the device is coupled with the upward, exhalation or air or gas extraction cycle of the device in a closed loop, thus preventing unassisted exhalation by the patient. The purpose of the latter embodiment is less to provide ventilation than it is to attempt to cause the lungs to so inflate and deflate as to keep the heart of the patient pumping.

U.S. Pat. No. 4,297,999 (the '999 patent) discloses a portable resuscitation apparatus comprising a rhythm apparatus for indicating the proper sequence or timing of compression and ventilation strokes, a head positioning means to assist in clearing the air or gas passages of the patient, and a mask which will fit most patients. The mask is secured to the patient's face by straps attached to the head positioning means, and air or gas is supplied from an associated remote bellows pump.

U.S. Pat. No. 4,493,614 (the '614 patent) discloses a pump for a portable ventilator. The pump is external to any ventilator apparatus in conjunction with which the pump is used.

U.S. Pat. No. 4,643,719 (the '719 patent) discloses a manually operated, bellows shaped aspirator for removing aspirated matter from the mouth and throat of a victim. Provision of ventilation air or gas is not part of the invention.

U.S. Pat. No. 4,782,831 (the '831 patent) discloses a complex, volume-controlled manual resuscitator. The device involves a system of three communicating chambers, with a balloon in the second chamber. A bulb is used to inflate a balloon to displace gas into the first chamber, thereby delivering to a patient a volume of gas proportional to the volume of gas displaced by the balloon. The third chamber receives ambient air or gas or supplied gas.

U.S. Pat. No. 4,836,198 (the '198 patent) discloses a portable ventilating device wherein a spring mounted in a cylinder opposes the motion of a piston which displaces gas into a patient's lungs. The device may be operated under gas-pressure or manually. However, there is no provision for adjusting the volume of the chamber, and the device thus can only provide a constant volume of gas at a constant rate. Further, it is required that the rescuer open and close external valves to initiate and end cycles.

U.S. Pat. No. 4,898,167 (the '167 patent) discloses an AIDS protection ventilation system comprising a variable volume spring loaded remote bellows pump, operated by the weight of a rescuer, for delivering air or gas to a patient. The remote pump of that system means that while the rescuer is creating a source of air-pressure with one hand remote from the patient, only one hand is available to secure the mask on the victim's face. Even worse, the system relies on a number of insert devices for use with the remote bellows pump the proper operation of which requires the non-pumping hand of the rescuer to time opening and closing of an orifice with a finger.

In a similar fashion to the summary of art found in the Background section of the U.S. Pat. No. 4,898,167 patent, in addition to the distinctions between the instant invention and the prior art devices and the shortcomings in those devices noted above, the following table summarizes some of the differences between some of the features and operation of the foregoing prior art devices and the UVD of the instant invention:

TABLE I

| Patent No. | Air or gas expulsion pressure controlled internal to device or remotely? | Both bands of rescuer participate in creating a seal on the victims face? | Ancillary rescuer activities required? | Unassisted victim exhalation? | Size? |
| --- | --- | --- | --- | --- | --- |
| UVD | Internal | yes | no | yes | small |
| '702 | Internal | no | no | no | large |
| '451 | Internal | no | yes | yes | small |
| '866 | External | no | no | no | large |
| '362 | External | no | yes | yes | large |
| '447 | External | N/A | N/A | yes | small |
| '830 | Internal | no | no | no | small |
| '999 | External | no | no | yes | small |

TABLE I-continued

| Patent No. | Air or gas expulsion pressure controlled internal to device or remotely? | Both bands of rescuer participate in creating a seal on the victims face? | Ancillary rescuer activities required? | Unassisted victim exhalation? | Size? |
| --- | --- | --- | --- | --- | --- |
| '614 | External | N/A | N/A | N/A | N/A |
| '719 | N/A | N/A | N/A | N/A | N/A |
| '831 | External | no | yes | yes | small |
| '198 | External | no | yes | yes | small |
| '167 | External | no | yes | yes | small |

BRIEF SUMMARY OF THE INVENTION

The universal ventilation device, UVD, of this invention is designed to separate the gas (and bodily fluids) of the victim from that of the rescuer and to deliver a known, adjustable volume of gas at a known, adjustable rate. The UVD can be used without other adjuncts, or in combination with a bag-valve device, or a compressed oxygen or compressed air or gas powered device.

Several embodiments of the basic invention are contemplated. FIGS. 1–5 are provided to illustrate the features of various embodiments, each of which can be made in adult or pediatric sizes, or in one size which is adjustable for both adult and pediatric use.

One end of the device is a standard face mask to be placed around the mouth and nose of the victim or patient. Alternatively, the mask can be removed and the device attached to an endotracheal tube. The device comprises a cylinder with a gas displacement means, such as a piston or bellows, deployed within the cylinder such that a preset volume of gas can be delivered. A positive pressure source, being either the lungs of a rescuer (FIGS. 1 and 2), or a traditional bag-valve device (which can be adapted for use with the devices of FIGS. 1 and 2), mechanical force (FIG. 3) or compressed gas power (FIGS. 4 and 5), is used to drive the piston or bellows. The volume of gas delivered to the patient is adjustable, for example, by use of a threaded "volume adjustment rod." In each of these embodiments, the rate of expiration by the rescuer, the mechanical rate of pressure transduction or the inherent impedance of the bellows or piston controls the flow-rate at which the gas can be delivered, and the rate of the spring recoil limits the respiratory rate (frequency) to that which is appropriate to the size (or weight) of the patient.

Accordingly, it is an object of this invention to provide a novel ventilation device that can be used with a plurality of different sources of air or gas for use on patients in need of resuscitation.

Another object of this invention is to provide a readily portable ventilation device which eliminates possible contact and exchange of fluids between patient and rescuer fluids which might otherwise be communicated in the course of ventilation.

Another object of this invention is to provide a readily portable ventilation device which delivers a regulated amount of air or gas to a recipient at a flow-rate that is helpful to the patient.

Other objects of the invention are apparent from the full disclosure.

BRIEF SUMMARY OF THE FIGURES

FIG. 2A is a schematic of a second, rescuer breath operated, embodiment of the UVD of the invention.

FIG. 2B is an exploded view of the second, rescuer-breath operated, embodiment of the invention.

DETAILED DESCRIPTION OF THE INVENTION

Figure 1:
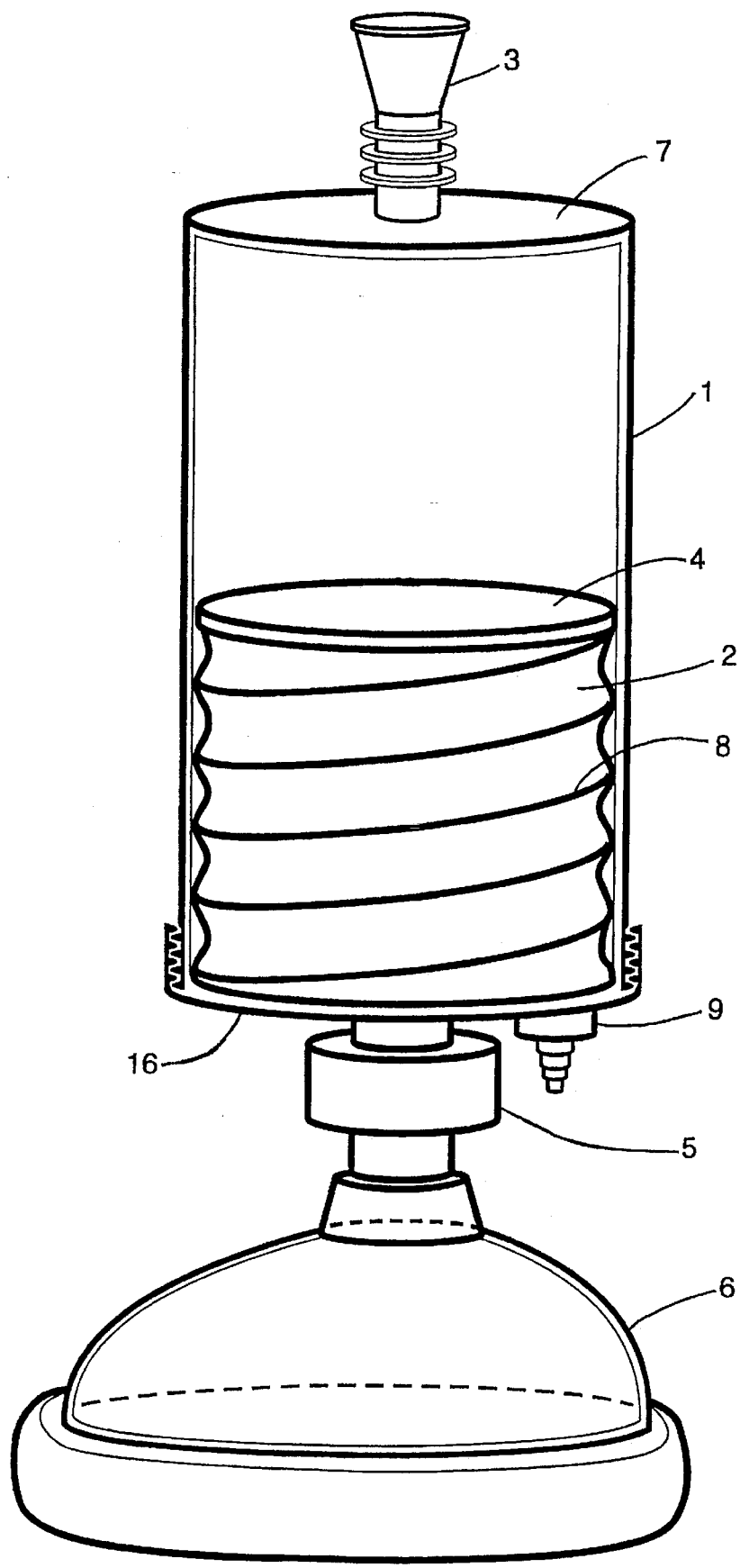
FIG. 1 is a schematic of a first, rescuer breath operated, embodiment of the UVD of the invention.

The term "Universal Ventilation Device" (UVD) is used herein to describe a device which may be used by anyone (universal), with minimal risk of injury, to assist people unable to breathe on their own. The term "Universal" as used herein is also intended to imply that the device is easily transportable and may be used with a variety of input gas sources. Thus, in various embodiments of this invention, the device may be operated by the power of a rescuer's own breath, by mechanical means, or the device may be linked to a source of compressed gas. Furthermore, it is also intended that the term "Universal" imply the general willingness to use the device by those that otherwise might fear contamination in the course of assisting others with conventional ventilation devices. Finally, the term "Universal" is intended to imply that the device is sufficiently simple and inexpensive that it could be made generally available to members of the public as well as to hospitals, mobile rescue teams such as Emergency Medical Services, and in doctors' offices.

The UVD of this invention has the following components, and the various embodiments described hereinbelow provide examples of the various components:

a) a rigid cylinder having an adjustable volume chamber for containing gas or air or gas to be delivered to a patient whose normal inspiration rate is interrupted or has ceased; the volume of the adjustable volume chamber may be adjusted to contain an amount of gas or air that is at least roughly equivalent to the lung tidal volume of the patient;

b) a rescuer-controlled expelling means for urging the gas or air from the adjustable volume chamber and into the lungs of a patient via a face-mask or endotracheal tube; the rescuer-controlled expelling means urges the gas or air from the adjustable volume chamber to enter the patient's lungs at a flow rate that is at least roughly matched to the normal inspiratory flow rate of the patient;

c) a double one-way patient valve located between the adjustable volume chamber and the face-mask or endotracheal tube which only allows the air or gas expelled from the adjustable volume chamber to enter the lungs of the patient while at the same time only allowing gas exhaled by the patient to vent to the atmosphere, rather than enter the adjustable volume chamber; and d) a one-way gas or air intake valve connected to the adjustable volume chamber which allows compressed gas or fresh air to enter the adjustable volume chamber when the rescuer-controlled expelling means is not urging air or gas into the lungs of the patient.

Preferably, a recoil mechanism, such as a spring, is provided which recoils at a rate that approximates the normal expiratory time of the victim and thus controls the respiratory rate (frequency) at which breaths are delivered.

The double one-way patient valve referred to in item (c) may be any means which accomplishes the desired goal of allowing gas exhaled from the patient to leave the face-mask or endotracheal tube, but which does not allow gas or air expelled from the adjustable volume chamber to leave without first entering the patient's lungs. Devices of this nature are now conventional in the art. Thus, for example, a duck-bill valve satisfies this function. Disposable versions of such valves are commercially available from Respironics, Inc., such as their VentEasy™ valve. In the specific embodiments described below, this element is referred to as a "double one-way patient valve" which is element 5 in the figures. In the description which follows, like parts or parts having similar functions are referred to by like numerals.

Figure 3:
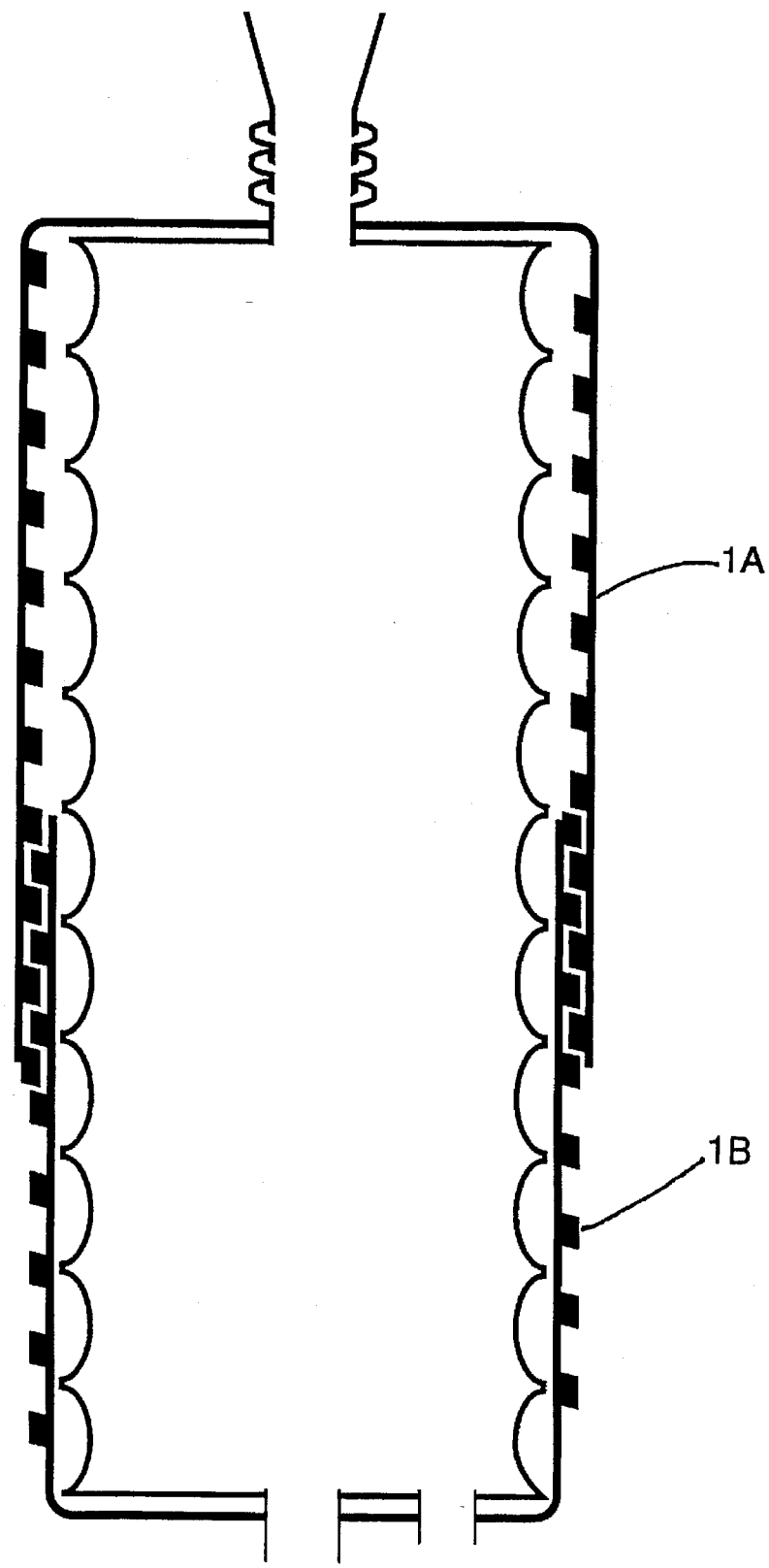
FIG. 3 is a sectional view of an embodiment in which the rigid cylinder comprises two matingly screwable sections which fit the one inside the other, to provide an adjustable volume, easily opened rigid cylinder.

Referring to FIG. 1, in a first embodiment of the UVD of this invention, there is provided a rigid cylinder 1 within which is deployed an adjustable volume chamber in the form of a flexible bellows 2. In FIG. 3, an embodiment of this invention is provided wherein the rigid cylinder is comprised of two matingly screwable sections 1A and 1B which fit, the one inside the other, such that volume is easily adjusted by screwing the one section in or out of the other. This type of cylinder could be used in any of the embodiments of this invention. A mouthpiece (preferably disposable) 3 is provided in and through the top 7 of the cylinder 1 for a rescuer to blow into the cylinder to act as the rescuer-controlled expelling means. As the rescuer exhales, a piston or plunger 4, which forms the upper surface of the bellows is slidably mounted within cylinder 1, and which may form a seal with the internal sides of the rigid cylinder, is forced to move downward. The volume of gas in the bellows is thereby displaced through a double one-way patient valve 5 at the other, bottom 16, end of the cylinder 1, and into the lungs of the victim via a face mask 6 or endotracheal tube. When positive pressure on the mouthpiece 3 is released by the rescuer, the patient exhales through the exhalation valve of the double one-way patient valve 5. As the bellows is urged to recoil by springs 8 which are mounted within the bellows and under the plunger 4, air or gas and/or supplemental oxygen fills the bellows through a one-way oxygen inlet/inhalation valve 9. In addition, the bellows springs 8 can be rated for tension in such a way that the rate of gas delivery is controlled by increasing spring tension as the bellows is increasingly depressed. The top 7 or the bottom 16 or both top and bottom of the cylinder may be removed by unscrewing or like means to allow replacement of the bellows 2, and cleanup of the internal surfaces of the cylinder 1. In this embodiment, in addition to adjusting volume according to the mechanism shown in FIG. 3, the volume may be adjusted by use of different sized (volume) bellows which could be chosen according to the age or weight of the victim, or the volume of any given bellows can be adjusted by bands, springs, chains, strings or like restrictive means.

Because the rate of air or gas inspiration by the patient is controlled in this embodiment by the rate of rescuer air or gas expiration, there is little danger that the rate of gas delivery will exceed the rate at which the patient's lungs can readily accept the air. In addition, if an adult rescuer is delivering air or gas to an adult patient, the volume of air or gas transferred will be roughly equivalent. Furthermore, because the volume of gas which can be contained within the bellows is adjustable by the rescuer to approximately match the age or weight of the recipient, the danger of overfilling the lungs and thereafter filling the stomach of the victim with air or gas is essentially eliminated. In addition to these advantages, this embodiment allows the rescuer to place both hands on the face mask 6 to completely seal the device on the face of the victim. Moreover, the gas delivered to the victim is entirely separate from that of the rescuer, which not only eliminates the risk of contamination, but also eliminates carbon dioxide from being introduced into the lungs of the patient. Furthermore, the rate of recoil of the bellows or springs below the piston can be selected to allow for sufficient time for exhalation and thereby limits the respiratory rate to that which is appropriate for the patient. Since small volumes (about 100–250 ml) are delivered to children at faster rates (about 16–24 breaths per minute) and larger volumes (about 500–1000 ml) are delivered to adults at slower rates (about 8–12 breaths per minute), the tension in the recoil spring can be adjusted or selected so that appropriate respiratory rates can be delivered according to the patient's size.

Referring now to FIG. 2A, in a second, rescuer-breath operated, embodiment of the UVD of this invention, there is provided a rigid cylinder 1 within which is deployed a flexible bellows 2B. This embodiment is the same as the above described embodiment in all respects except that this embodiment, an internal volume set means 10 is provided. This can be a volume set screw or any other means whereby the full expansion of the bellows 2B induced by the springs 8 is limited to any desired volume. In addition, through the top 7 of the cylinder, a rod or tube 21 is deployed, the end of which is affixed to the top 7 of the cylinder. The rod or tube 21 does not restrict the flow of gas blown into the chamber 2A. Thus, gas exhaled into the cylinder 1 creates pressure in the chamber 2A, thereby forcing the bellows forming chamber 1B to expel gas contained therein through the valve 5.

The amount of air that can be contained in the bellows is controlled by the operator during assembly by simply loosening and tightening the volume set screw 10 at a marking 11 on the tube or rod 21 for any desired volume. Assembly of the unit is shown in the exploded view of FIG. 2B. At the end of the tube that fits into the bottom of the inside of the bellows, the tube sits inside a depression 23 such that it remains in place, providing a stable central guide for the bellows. The depression 23 must be large enough to accommodate the tube, while at the same time allowing gas contained within the bellows to escape around the tube and enter the valve 5. The advantage of this embodiment of the invention is that only one bellows 2 need be provided, the volume of which may be controlled easily via the volume set screw. In addition, the rod or tube 21 provides a central guide to ensure straight up and down movement of the top seal 4 of the bellows.

Figure 4:
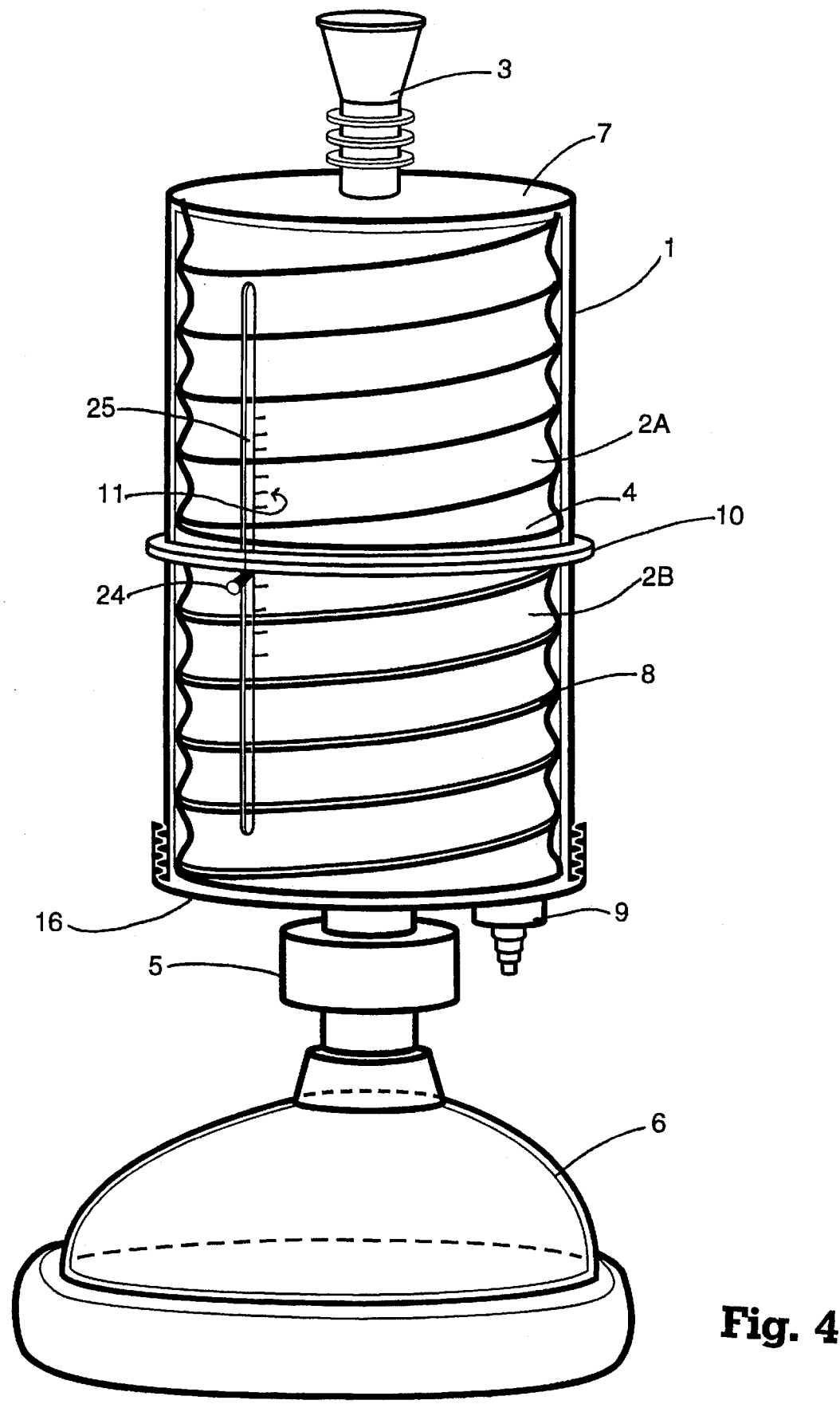
FIG. 4 is a schematic of a third, rescuer-breath operated, embodiment of the UVD of the invention.

Referring now to FIG. 4, in a third embodiment of the UVD of this invention, there is provided a rigid cylinder 1 within which is deployed a flexible bellows 2. A novel unitary bellows is provided in this embodiment in which there are two chambers, 2A, and 2B, separated by a membrane, plunger, piston, or like divider 4. The upper chamber 2A is open to the mouthpiece (preferably disposable) 3, which operates as described above for the first embodiment. However, in this embodiment, as the rescuer exhales, the upper bellows chamber 2A fills with the exhaled gas. This forces the lower chamber 2B to expel entrained gas through the double one-way patient valve 5 at the other end of the cylinder, and into the lungs of the victim via a face mask 6 or endotracheal tube. When positive pressure on the mouthpiece 3 is released by the rescuer, the patient exhales through the exhalation valve of the double one-way patient valve 5. As the bellows in the lower chamber 2B is urged to recoil by springs 8 which are mounted within the bellows and under the plunger 4, air or gas and/or supplemental oxygen fills the bellows through a one-way oxygen inlet/inhalation valve 9. A volume set ring 10, which is slidably mounted on the outside of the cylinder 1 allows the rescuer to match the volume of air or gas that can be contained in the lower chamber 2B of the bellows when fully inflated to calibration marks 11 provided on the cylinder for different ages or weights of patients. The travel and therefore volume in chamber 2B is limited by the volume set ring due to tabs 24 on the bellows plate 4 that extend from at least 2 sides of the bellows plate 4 and are trapped by the volume set ring 10. The tabs 24 on the bellows plate 4 ride in a groove 25 on at least two sides of the rigid cylinder 1. In this embodiment, it is not necessary for the bellows plate 4 to form a seal with the internal sides of the rigid cylinder, as the entire bellows 2 is a unitary, sealed element that does not depend on the plunger or bellows plate to create a closed system.

The advantages in this embodiment are that the entire bellows 2 can be a sealed, disposable unit such that after each use of the UVD, the disposable unit may be appropriately discarded, after removing either the top 7, the bottom 16, or both the top and bottom of the cylinder 1, a new bellows inserted, and the UVD could be ready for service on a new patient very quickly. Naturally, the face mask 6 and rescuer mouthpiece 3 should also be replaced or at least cleaned between uses by different rescuers or on different patients. It should be noted that in any of the aforesaid embodiments, the mouthpiece 3 may be adapted for use with either a compressed gas source or a mechanical pump, such as a hand or foot operated bulb or like pumping device, so long as the flow rate and volume of air or gas delivery to the patient is at least roughly equivalent to those found with the normal rate of inspiration.

Figure 5:
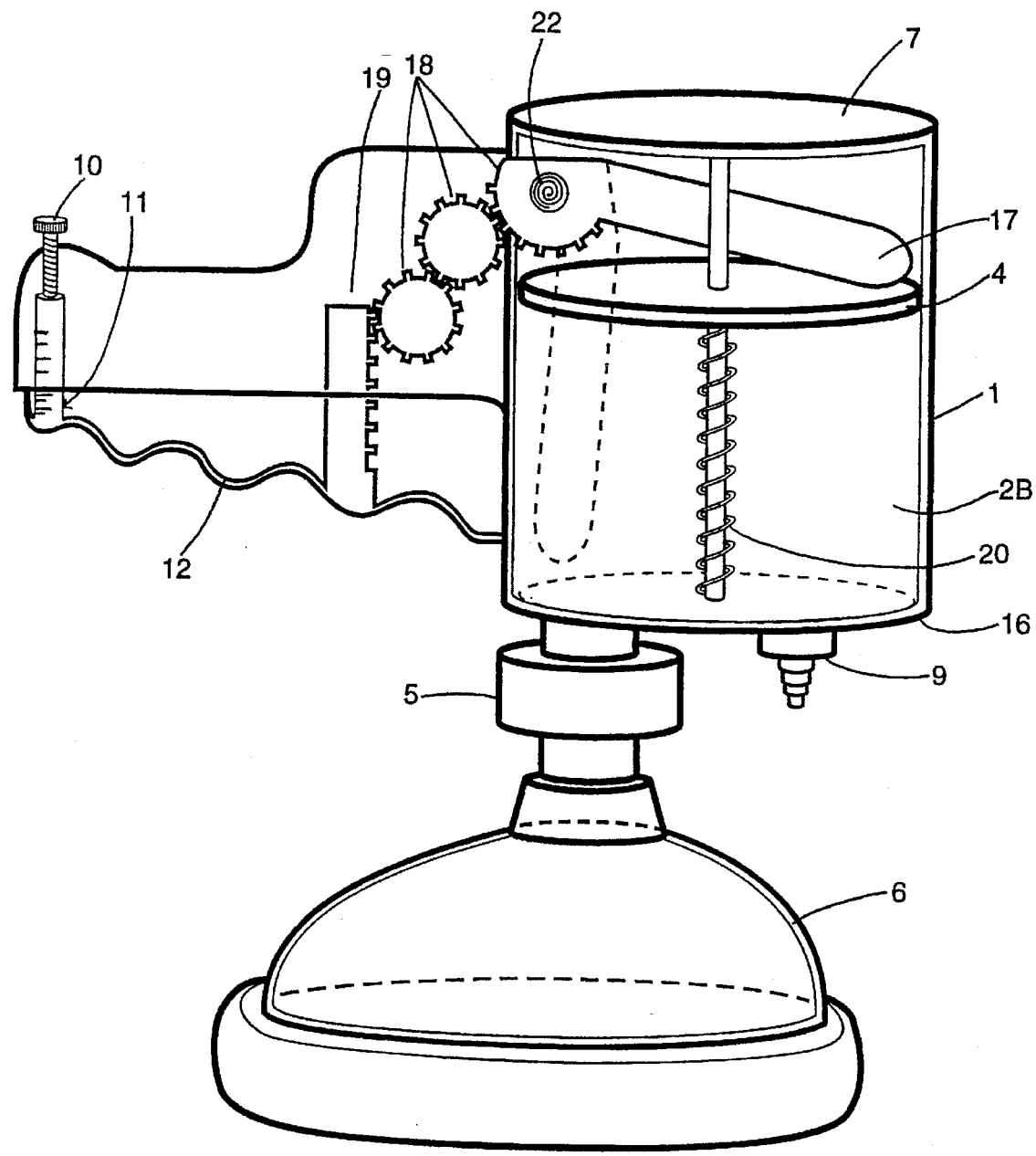
FIG. 5 is a schematic of a fourth mechanically operated, embodiment of the UVD of the invention.

Referring now to FIG. 5, a fourth embodiment of the UVD of this invention is illustrated wherein there is provided a rigid cylinder 1 within which is a chamber 2B having a volume defined by the sides of the cylinder 1 and a piston 4. Within the chamber 2B a flexible bellows may be deployed, or the gas within the chamber may be contained by the piston 4 which forms a seal with the walls of the cylinder as in the first embodiment described hereinabove. In place of the mouthpiece 3 of the foregoing embodiments, a volume controller 10 and piston positioning means 17 are provided which may be set to regulate the volume of the chamber 2B, whereby the rescuer is able to match the volume of air or gas that can be contained in the chamber 2B or the bellows within chamber 2B when fully inflated, using calibration marks 11 provided on the volume controller 10 for different ages or weights of recipients. The volume controller 10 defines the position of arm 17 or like piston 4 positioning means. The arm 17 is maintained in contact with the piston 4 by means of an arm-biasing means such as by the spring 22. Force to expel the gas entrained in chamber 2B is provided in this embodiment by a mechanical pressure device, such as the hand-grip 12. As the hand-grip 12 is squeezed by an operator, the piston 4 is forced downward by the arm 17 to expel entrained gas in chamber 2B through the double one-way patient valve 5 at the other end of the cylinder, and into the lungs of the victim via a face mask 6 or endotracheal tube. Depression of the hand grip 12 causes a series of gears 18 to be driven by a ratchet 19 within the handle, causing the arm 17 to force the piston 4 toward the patient, thereby expelling gas entrapped in chamber 2B. The volume adjustment means 10 limits the distance that piston 4 can be urged to return by spring 20, thereby limiting the volume of chamber 2B according to markings 11 matching the age or weight of the victim to the volume. The spring 20 and piston 4 ride on a central tube 26, which keeps the piston moving straight up and down within the cylinder. The rate of gas expulsion can be directly related to the rate at which the hand-grip is activated. It may also be regulated by the progressive resistance provided by spring 20. When positive pressure on the hand-grip 12 is released by the rescuer, the patient exhales through the exhalation valve of the double one-way patient valve 5. As the piston or bellows in the chamber 2 is urged to recoil by springs 20 mounted within the chamber 2B below the piston 4 or within a bellows optionally deployed within chamber 2B under the piston 4, air or gas and/or supplemental oxygen fills the chamber 2B or bellows through a one-way gas inlet/inhalation valve 9.

The advantages in this embodiment are that the mechanical hand-grip actuation of positive displacement pressure completely avoids any danger of cross-contamination between the rescuer and the recipient. Further, it avoids rescuer fatigue and possible hyperventilation by the rescuer. In addition, due to the novel design of this embodiment, even though only one hand is available to place pressure on the face mask 6, the hand pumping the mechanical hand-grip 12 is also able to provide downward sealing pressure. This is achieved by the expedient of off-setting the placement of the double one-way patient valve 5 from the center of the bottom 16 of the cylinder. In addition, it is important that the hand-grip 12 be placed as close as possible to the face-mask 6. By virtue of the eccentric placement of the double one-way patient valve 5 and the low placement of the hand-grip 12, substantial downward sealing pressure may be applied by the pumping hand, while the other hand of the operator may be placed directly on the face-mask 6 to generate a tight seal.

Figure 6A:
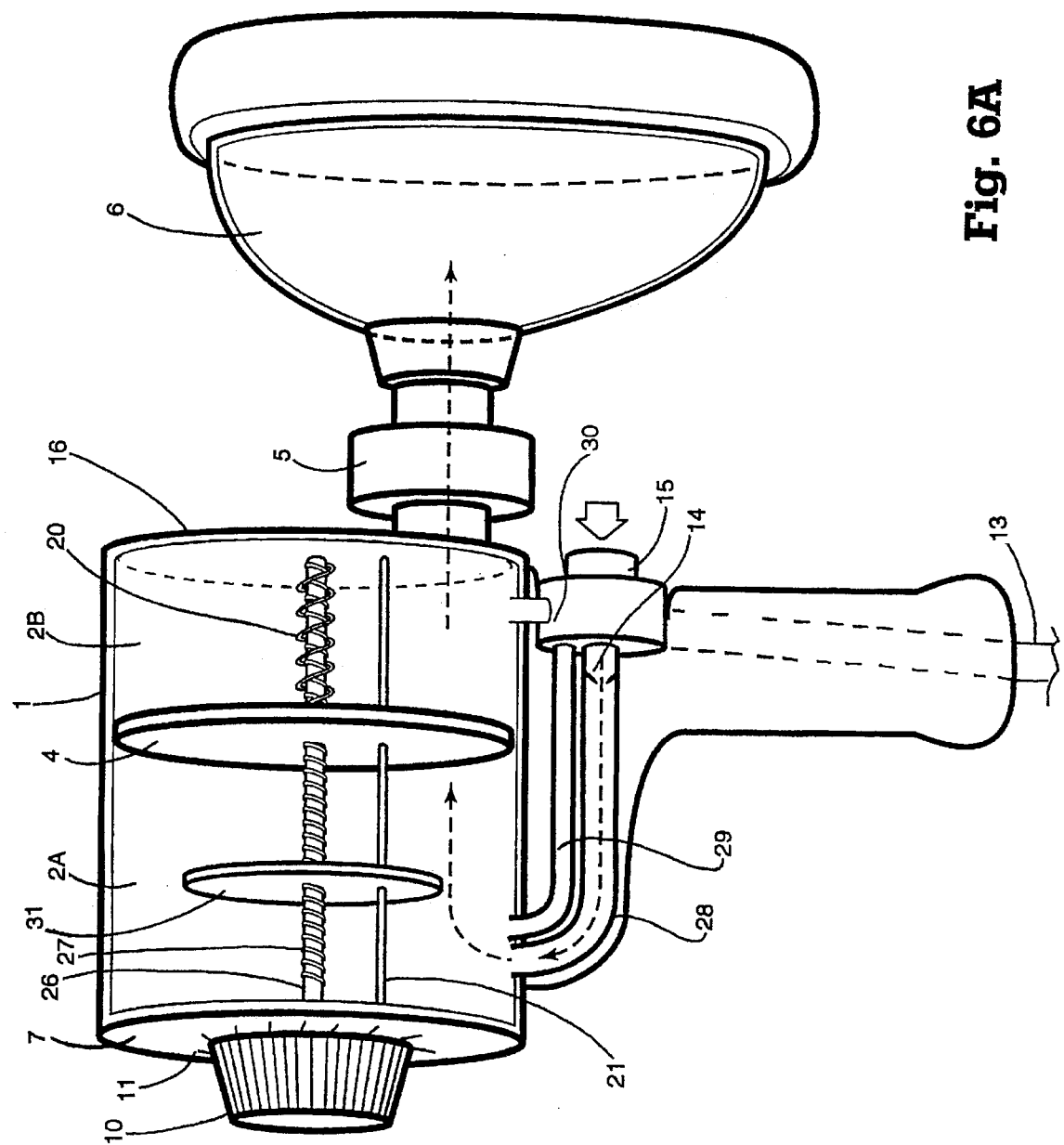
FIG. 6A is a schematic of a fifth, compressed-gas operated, embodiment of the UVD of the invention.

Referring now to FIG. 6A, a compressed gas (such as oxygen) powered breathing device is shown which can be used to deliver gas to a patient in need. This device is similar to the embodiment shown in FIG. 5, except that in this device, a source of compressed gas is fed into the device via an inlet hose 13. Entrance of gas is regulated by a valve 14 which may have a button 15 or like actuator for the operator to control incoming compressed gas. Air or gas or compressed oxygen is pumped in through the one-way valve 14 through conduit 28 and fills the chamber 2A, forcing the bellows or piston 4 downward, which sends the set volume of oxygen or air or gas contained within chamber 2B through the double one-way patient valve 5. During this phase of operation, a valve 30 is closed. The volume is set by volume control means 10 which is set to any desired volume according to markings 11. As the dial 10 is turned, a volume set plate 31 is caused to move upward or downward, thereby restricting the maximum volume of chamber 2B defined by piston 4. A guide tube 21 runs through the volume set plate 31 and piston 4 such that these members move straight up and down within the cylinder 1 and so that as the dial 10 is adjusted, the volume set plate 31 is caused to move up or down the central tube 26 which may have a thread 27 to force the volume set plate to translate. The rate at which gas is delivered to the patient is controlled by the flow-rate of the oxygen powered breathing device, and by the spring 20 which provides progressively increasing resistance toward the end of each "breath". After the "breath" is delivered, the spring 20 urges the piston 4 to return to the set volume position. The rate at which the spring 20 returns the plate 4 to the volume set plate 31 determines the ventilation rate. For children, the plate would travel a shorter distance due to the smaller tidal volume than adults, thus the respiratory rate (frequency) can be relatively fast. In adults, the piston travel would be greater and thus the respiratory rate would be slower. The actuator 15 is released and the valve 30 opens while the valve 14 closes to allow the compressed oxygen or air that filled chamber 2A to be displaced and to enter the chamber 2B, through conduit 29, as shown in FIG. 6B, as the spring 20 biases the piston 4 to return toward the volume set plate 31.

Figure 6B:
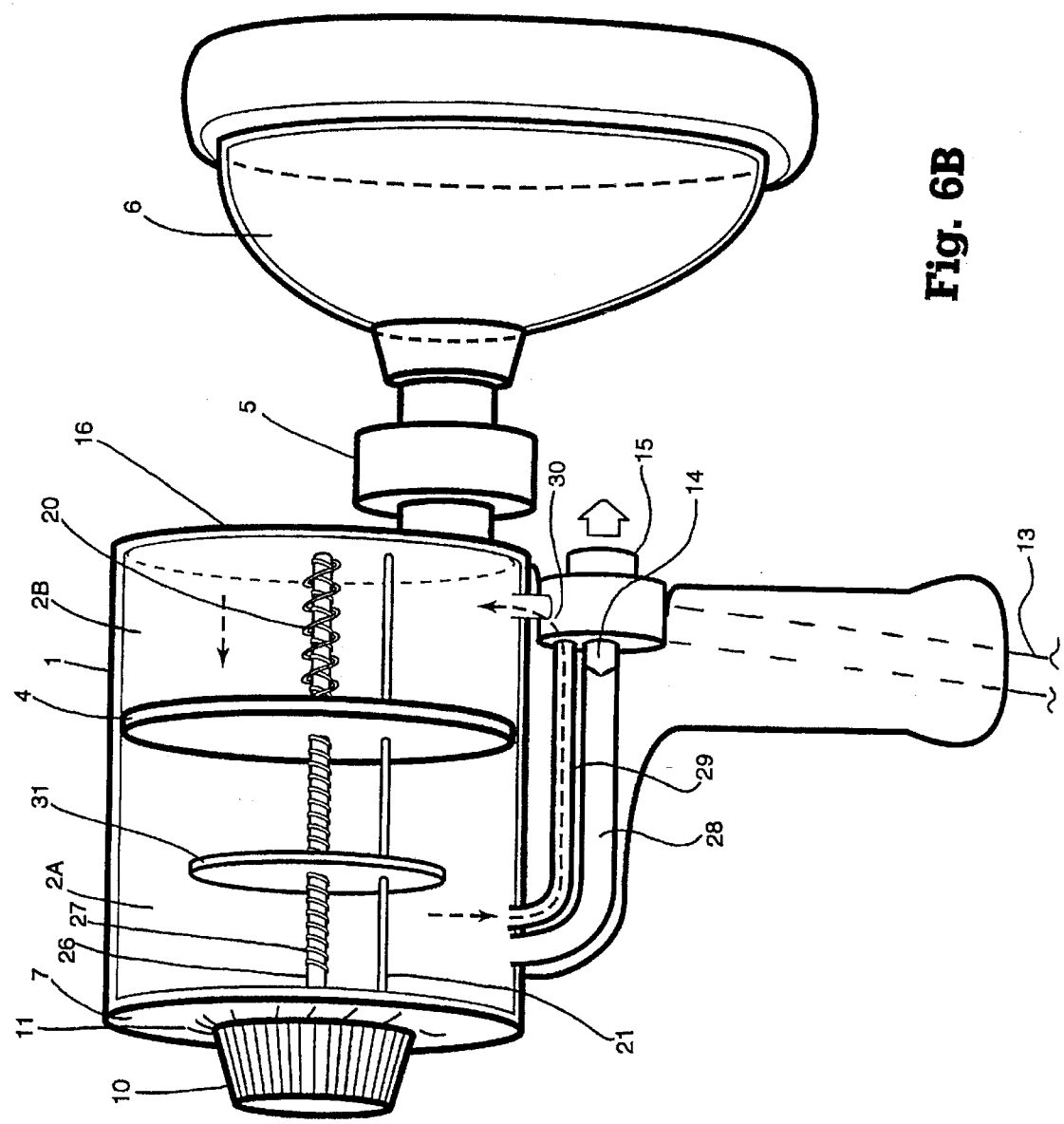
FIG. 6B is a schematic of the gas flow in the fifth, compressed-gas operated, embodiment of the UVD of the invention.

Referring now to FIG. 6B, as the button 15 or like actuator for the operator to control incoming compressed gas is released, the spring 20 urges the plate 4 to move back to the maximum volume set by plate 31. Gas from chamber 2A vents into chamber 2B through the now open valve 30 and conduit 29, and is thus available for delivery to the patient when the actuator 15 is next depressed. The cycle is then repeated as needed. This embodiment saves compressed gas by using it first as the means for displacement, and then second, as the gas delivered to the patient.

In regular use on an adult, this embodiment may preferably be operated within the following approximate specifications:

| Inspiratory flow rate, | $V_I$ | - | about 30 L/min. (1.0 L in 2.0 sec.) |
|---|---|---|---|
| Tidal volume, | $V_T$ | - | about 0.5–1.0 L |
| Inspiratory time, | $T_I$ | - | about 2.0 sec. |
| Expiratory time, | $T_E$ | - | about 4.0 sec. |
| Frequency, | | - | about 10 breaths per minute |

Peak pressure limit (cessation of flow) can be limited at 60–80 cm $H_2O$ above the pressure required to move the piston.

These parameters can be adjusted as appropriate for age, size or weight.

The advantages of this embodiment of the UVD are that the flow of gas, and thus the duration of inhalation, can be precisely controlled by the flow rate of the input gas. The UVD used in combination with valves 14 and 30 results in an apparatus that has most of the characteristics, aside from the ability to precisely control the frequency of breaths (which is done manually by the rescuer), of sophisticated and expensive automatic transport ventilators (ATVs). Thus, this embodiment of the UVD offers an inexpensive alternative to ATVs. The UVD is expected to be used predominantly by people who are not trained in the use of the ATV and by agencies that cannot afford the ATV.

While the foregoing description of the invention and examples of specific embodiments thereof provides disclosure of how to make and use the UVD of this invention, including its best mode, it should be understood that equivalents and obvious variations of the specifics disclosed herein form an integral part of this invention. Thus, for example, it should be noted that a balloon may be used instead of the piston. It is also possible to use disposable bags at either end of the device, which would facilitate cleaning. Thus, the scope of this invention should be defined with reference to the claims appended hereto rather than from the specifics described hereinabove.

REFERENCES

Lyon, Edward H., U.S. Pat. No. 1,371,702, issued Mar. 15, 1921.

Emerson, John H., U.S. Pat. No. 2,428,451, issued Oct. 7, 1947.
Ritchie, David, U.S. Pat. No. 3,461,866, issued Aug. 19, 1969.
Eyrick, Theodore B., Allen C. Brown, Neil R. Hattes, U.S. Pat. No. 3,905,362, issued Sep. 16, 1975.
Inkster, John S., Norman Burn, U.S. Pat. No. 3,918,447, issued Nov. 11, 1975.
da Costa, Harry, U.S. Pat. No. 3,939,830, issued Feb. 24, 1976.
Kitrell, John V., U.S. Pat. No. 4,297,999, issued Nov. 3, 1981.
Chu, Raymond D., Marc A. Bergman, U.S. Pat. No. 4,493,614, issued Jan. 15, 1985.
Garth, Geoffrey C., Charles A. Patterson, U.S. Pat. No. 4,643,719, issued Feb. 17, 1987.
Gallant, John H., U.S. Pat. No. 4,782,831, issued Nov. 8, 1988.
Gates, William M., U.S. Pat. No. 4,836,198, issued Jun. 6, 1989.
Pierce, Richard S., Willem J. Van Leeuwen, U.S. Pat. No. 4,898,167, issued Feb. 6, 1990.

I claim:

1. A universal ventilation device comprising:
   a) a rigid cylinder having a top, bottom and having an adjustable volume chamber therein for containing gas or air to be delivered to a patient whose normal inspiration rate is interrupted or has ceased; said rigid cylinder further including means for connecting said top and bottom and a means for adjusting the volume of the adjustable volume chamber; wherein at least one of said means for connecting or said means for adjusting is employed to adjust a volume of gas or air delivered to a patient to be roughly equivalent to such a patient's lung tidal volume;
   b) a rescuer-controlled expelling means for urging the gas or air from said adjustable volume chamber and into a patient's lungs via a face-mask or endotracheal tube, wherein said rescuer-controlled expelling means urges said gas or air from said adjustable volume chamber to enter a patient's lungs at a flow rate that is at least roughly matched to the normal inspiratory flow rate of a patient;
   c) a double one-way patient valve located between said adjustable volume chamber and said face-mask or said endotracheal tube which only allows the air or gas expelled from the adjustable volume chamber to enter a patient's lungs and which allows gas exhaled by a patient to vent to the atmosphere, but does not allow air or gas exhaled by a patient to enter said adjustable volume chamber; and
   d) a one-way gas or air intake valve connected to said adjustable volume chamber which allows compressed gas or fresh air to enter said adjustable volume chamber when said rescuer-controlled expelling means is not urging air or gas into a patient's lungs.

2. The universal ventilation device of claim 1 further comprising a return means for returning said expelling means to reestablish the full volume of said adjustable volume chamber after said gas or air is expelled, wherein said return means reestablishes said full volume at a rate which allows the device to cycle at a frequency which approximates a patient's normal inhalation and exhalation rate.

3. The universal ventilation device of claim 2 wherein said rescuer-controlled expelling means comprises:
   a) a mouthpiece situated at the top of said rigid cylinder into which the rescuer can exhale;
   b) a plunger or piston slidably and sealably mounted within said rigid cylinder at the top of and partially defining said adjustable volume chamber, said piston or plunger being forced to move downward as a rescuer exhales into the mouthpiece; and
   c) a resilient balloon or recoil spring mounted bellows, the internal space of which is interconnected with said one-way gas or air intake valve, wherein said resilient balloon or recoil spring mounted bellows is located below said plunger or piston, and with said piston, defining the remainder of said adjustable volume chamber, such that when the plunger or piston is forced to move downward, gas or air contained within the adjustable volume chamber is forced to move through said double one-way patient valve and into a patient's lungs.

4. The universal ventilation device of claim 3 wherein the volume of said adjustable volume chamber is adjusted by inserting bellows of different volumes into said rigid cylinder.

5. The universal ventilation device of claim 3 wherein the volume of said adjustable volume chamber is adjusted by means of a volume set screw riding on a tube through the center of said bellows.

6. A universal ventilation device comprising:
   a) a rigid cylinder having an adjustable volume chamber for containing gas or air to be delivered to a patient whose normal inspiration rate is interrupted or has ceased, wherein said adjustable volume chamber may be adjusted to contain an amount of gas or air that is at least roughly equivalent to the lung tidal volume of a patient;
   b) a rescuer-controlled expelling means for urging the gas or air from said adjustable volume chamber and into a patient's lungs via a face-mask or endotracheal tube, wherein said rescuer-controlled expelling means urges said gas or air from said adjustable volume chamber to enter a patient's lungs at a flow rate that is at least roughly matched to the normal inspiratory flow rate of a patient;
   c) a double one-way patient valve located between said adjustable volume chamber and said face-mask or said endotracheal tube which only allows the air or gas expelled from the adjustable volume chamber to enter a patient's lungs and which allows gas exhaled by a patient to vent to the atmosphere, but does not allow air or gas exhaled by a patient to enter said adjustable volume chamber;
   d) a one-way gas or air intake valve connected to said adjustable volume chamber which allows compressed gas or fresh air to enter said adjustable volume chamber when said rescuer-controlled expelling means is not urging air or gas into a patient's lungs;
   e) said rescuer-controlled expelling means including a mouthpiece situated at the top of said rigid cylinder into which a rescuer can exhale; and
   f) said rescuer-controlled expelling means including a two chamber bellows having an upper and a lower chamber wherein said lower chamber is located below a divider which separates the volumes of said upper and said lower chambers from each other, the internal space of said lower chamber being interconnected with said one-way gas or air intake valve, said upper chamber forming a collapsible chamber into which the rescuer exhales through the mouthpiece, whereupon said upper chamber expands in volume, forcing the lower chamber, which forms the adjustable volume chamber, to expel as or air contained therein as a result of intake induced by a recoil spring mounted in the lower chamber of said two chamber bellows, through the double one-way patient valve and into a patient's lungs.

7. A universal ventilation device comprising:
a) a rigid cylinder having an adjustable volume chamber for containing gas or air to be delivered to a patient whose normal inspiration rate is interrupted or has ceased, wherein said adjustable volume chamber may be adjusted to contain an amount of gas or air that is at least roughly equivalent to the lung tidal volume of a patient;
b) a rescuer-controlled expelling means for urging the gas or air from said adjustable volume chamber and into a patient's lungs via a face-mask or endotracheal tube, wherein said rescuer-controlled expelling means urges said gas or air from said adjustable volume chamber to enter a patient's lungs at a flow rate that is at least roughly matched to the normal inspiratory flow rate of a patient;
c) a double one-way patient valve located between said adjustable volume chamber and said face-mask or said endotracheal tube which only allows the air or gas expelled from the adjustable volume chamber to enter a patient's lungs and which allows gas exhaled by a patient to vent to the atmosphere, but does not allow air or gas exhaled by a patient to enter said adjustable volume chamber;
d) a one-way gas or air intake valve connected to said adjustable volume chamber which allows compressed gas or fresh air to enter said adjustable volume chamber when said rescuer-controlled expelling means is not urging air or gas into the lungs of a patient;
e) said rescuer-controlled expelling means including a handle-grip affixed to the external wall of said rigid cylinder toward the base of the cylinder which is pumped or squeezed by a rescuer's hand; and
f) said rescuer-controlled expelling means including a piston or plunger which is forced downward as the handle-grip is pumped or squeezed, wherein said piston is slidably and sealably affixed within the internal volume of said rigid cylinder such that upon moving downward, air or gas trapped below the piston or plunger is forced to leave the chamber formed by the piston and the internal walls of the cylinder through the double one-way patient valve and into a patient's lungs.

8. A universal ventilation device comprising:
a) a rigid cylinder having an adjustable volume chamber for containing gas or air to be delivered to a patient whose normal inspiration rate is interrupted or has ceased, wherein said adjustable volume chamber may be adjusted to contain an amount of gas or air that is at least roughly equivalent to the lung tidal volume of a patient;
b) a rescuer-controlled expelling means for urging the gas or air from said adjustable volume chamber and into a patient's lungs via a face-mask or endotracheal tube, wherein said rescuer-controlled expelling means urges said gas or air from said adjustable volume chamber to enter a patient's lungs at a flow rate that is at least roughly matched to the normal inspiratory flow rate of a patient;
c) a double one-way patient valve located between said adjustable volume chamber and said face-mask or said endotracheal tube which only allows the air or gas expelled from the adjustable volume chamber to enter a patient's lungs and which allows gas exhaled by a patient to vent to the atmosphere, but does not allow air or gas exhaled by a patient to enter said adjustable volume chamber;
d) one-way gas or air intake valve connected to said adjustable volume chamber which allows compressed gas or fresh air to enter said adjustable volume chamber when said rescuer-controlled expelling means is not urging air or gas into the lungs of a patient;
e) said rescuer-controlled expelling means including a handle-grip affixed to the external wall of said rigid cylinder toward the base of the cylinder;
f) said rescuer-controlled expelling means including a rescuer operable gas control valve mounted in said handle-grip to which a source of compressed air or gas is attached through an inlet line; and
g) said rescuer-controlled expelling means including a piston or plunger which is forced downward as a rescuer activates the gas control valve to allow compressed gas to enter the rigid cylinder above the piston or plunger, wherein said piston or plunger is slidably and sealably affixed within the internal volume of said rigid cylinder such that upon moving downward, air or gas trapped below the piston or plunger is forced to leave the chamber formed by the piston and the internal walls of the cylinder through the double one-way patient valve and into a patient's lungs.

9. The universal ventilation device of claim 8 wherein the gas in the rigid chamber above the piston moves to the chamber below the piston after said rescuer releases said gas control valve.

10. The universal ventilation device of claim 8 wherein, in regular use on an adult, the device is operated within the following specifications:

| | | |
|---|---|---|
| Inspiratory flow rate, | $V_I$ - | about 30 L/min. (1.0 L in 2.0 sec.) |
| Tidal volume, | $V_T$ - | about 0.5–1.0 L |
| Inspiratory time, | $T_I$ - | about 2.0 sec. |
| Expiratory time, | $T_E$ - | about 4.0 sec. |
| Frequency, | - | about 10 breaths per minute | pressure limit set at about 60–80 cm $H_2O$ above the pressure required to move the piston.

11. A universal ventilation device comprising:
a) a rigid cylinder having an adjustable volume chamber for containing gas or air to be delivered to a patient whose normal inspiration rate is interrupted or has ceased, wherein said adjustable volume chamber may be adjusted to contain an amount of gas or air that is at least roughly equivalent to the lung tidal volume of a patient wherein said rigid cylinder comprises two matingly threaded sections which can be screwed into or out of each other to thereby adjust the total volume of gas that can be contained within said rigid cylinder;
b) a rescuer-controlled expelling means for urging the gas or air from said adjustable volume chamber and into a patient's lungs via a face-mask or endotracheal tube, wherein said rescuer-controlled expelling means urges said gas or air from said adjustable volume chamber to enter a patient's lungs at a flow rate that is at least roughly matched to the normal inspiratory flow rate of a patient;
c) a double one-way patient valve located between said adjustable volume chamber and said face-mask or said endotracheal tube which only allows the air or gas expelled from the adjustable volume chamber to enter a patient's lungs and which allows gas exhaled by a patient to vent to the atmosphere, but doe not allow air or gas exhaled by a patient to enter said adjustable volume chamber;

d) a one-way gas or air intake valve connected to said adjustable volume chamber which allows compressed gas or fresh air to enter said adjustable volume chamber when said rescuer-controlled expelling means is not urging air or gas into the lungs of a patient.

* * * * *

UNITED STATES PATENT AND TRADEMARK OFFICE
CERTIFICATE OF CORRECTION

PATENT NO. : 5,628,305
DATED : May 13, 1997
INVENTOR(S) : Richard Melker

It is certified that error appears in the above-indentified patent and that said Letters Patent is hereby corrected as shown below:

Column 7, line 38: "forming chamber 1B" should read --forming chamber 2B--.

Signed and Sealed this

Second Day of September, 1997

Attest:

BRUCE LEHMAN

Attesting Officer

Commissioner of Patents and Trademarks